United States Patent
Burnam et al.

(10) Patent No.: US 12,350,495 B2
(45) Date of Patent: Jul. 8, 2025

(54) METHOD OF TREATMENT OF DRUG RESISTANT HYPERTENSION

(71) Applicant: BaroPace, Inc., Ashland, OR (US)

(72) Inventors: Michael Burnam, Ashland, OR (US); Eli Gang, Los Angeles, CA (US)

(73) Assignee: BaroPace, Inc., Ashland, OR (US)

( * ) Notice: Subject to any disclaimer, the term of this patent is extended or adjusted under 35 U.S.C. 154(b) by 275 days.

(21) Appl. No.: 17/907,344

(22) PCT Filed: Aug. 3, 2020

(86) PCT No.: PCT/US2020/044784
§ 371 (c)(1),
(2) Date: Sep. 26, 2022

(87) PCT Pub. No.: WO2021/194543
PCT Pub. Date: Sep. 30, 2021

(65) Prior Publication Data
US 2023/0145292 A1    May 11, 2023

Related U.S. Application Data (63) Continuation-in-part of application No. PCT/US2020/025447, filed on Mar. 27, 2020, and a
(Continued)

(51) Int. Cl.
*A61N 1/00* (2006.01)
*A61N 1/362* (2006.01)
*A61N 1/365* (2006.01)

(52) U.S. Cl.
CPC ......... *A61N 1/3627* (2013.01); *A61N 1/3628* (2013.01); *A61N 1/36564* (2013.01)

(58) Field of Classification Search
None
See application file for complete search history.

(56) References Cited

U.S. PATENT DOCUMENTS

| | | |
|---|---|---|
| 4,791,931 A | 12/1988 | Slate |
| 5,129,394 A | 7/1992 | Mehra |

(Continued)

FOREIGN PATENT DOCUMENTS

| | | |
|---|---|---|
| CA | 2195018 A1 | 2/1996 |
| CN | 203494057 U | 3/2014 |

(Continued)

OTHER PUBLICATIONS

International Search Report and Written Opinion in International Application No. PCT/US19/59703, mailed Feb. 25, 2020 (7 pages).

(Continued)

*Primary Examiner* — Sana Sahand
(74) *Attorney, Agent, or Firm* — Bookoff McAndrews, PLLC (57) ABSTRACT

A method of right atrial pacing of a heart of a patient includes the steps of: stimulating right atrial tissue of the heart using a right atrial lead of a dual chamber cardiac pacemaker to pace the heart with a stimulus architecture protocol; and stimulating local sympathetic and/or parasympathetic tissues with the stimulus architecture protocol proximate to the paced right atrial tissue causing nervous system activity that inhibits the autonomous nervous system to reduce blood pressure. A closed loop system operating according to this method and a cardiac pacing lead for implementing this method also are included within the scope of the illustrated embodiments.

15 Claims, 4 Drawing Sheets

Related U.S. Application Data continuation-in-part of application No. PCT/US2019/059703, filed on Nov. 4, 2019.

(60) Provisional application No. 63/101,544, filed on May 5, 2020, provisional application No. 62/833,052, filed on Apr. 12, 2019, provisional application No. 62/757,559, filed on Nov. 8, 2018.

(56) References Cited

U.S. PATENT DOCUMENTS

| | | | |
|---|---|---|---|
| 5,304,209 A | | 4/1994 | Adams et al. |
| 5,904,708 A | | 5/1999 | Goedeke |
| 6,141,590 A | | 10/2000 | Renirie et al. |
| 6,662,047 B2 | | 12/2003 | Sorensen et al. |
| 7,460,899 B2 | | 12/2008 | Almen |
| 7,660,628 B2 | | 2/2010 | Libbus et al. |
| 7,949,398 B1 | * | 5/2011 | Wenzel ............... A61N 1/36117 607/42 |
| 8,046,070 B2 | | 10/2011 | Salo et al. |
| 8,086,315 B2 | | 12/2011 | Schwartz et al. |
| 8,112,150 B2 | | 2/2012 | Naqvi et al. |
| 8,509,893 B2 | | 8/2013 | Xiao et al. |
| 8,836,535 B2 | | 9/2014 | Zhang et al. |
| 9,005,130 B2 | | 4/2015 | Fischell et al. |
| 9,155,479 B2 | | 10/2015 | Solem |
| 9,636,513 B2 | | 5/2017 | Kuo et al. |
| 9,943,263 B2 | | 4/2018 | Lee |
| 9,955,289 B1 | | 4/2018 | Liu et al. |
| 10,052,494 B2 | | 8/2018 | Sheldon et al. |
| 2004/0049235 A1 | | 3/2004 | Deno et al. |
| 2006/0064134 A1 | | 3/2006 | Mazar et al. |
| 2006/0217772 A1 | * | 9/2006 | Libbus ............... A61N 1/36057 607/9 |
| 2007/0142864 A1 | * | 6/2007 | Libbus ............... A61N 1/36542 607/2 |
| 2007/0260285 A1 | | 11/2007 | Libbus et al. |
| 2007/0299477 A1 | | 12/2007 | Kleckner et al. |
| 2011/0213435 A1 | | 9/2011 | Rom |
| 2014/0350630 A1 | | 11/2014 | Rosenberg et al. |
| 2016/0175595 A1 | | 6/2016 | Lian et al. |
| 2016/0198996 A1 | | 7/2016 | Dullen |
| 2016/0220824 A1 | | 8/2016 | Schwartz et al. |
| 2016/0279432 A1 | | 9/2016 | Chappel |
| 2017/0304048 A1 | | 10/2017 | Mika et al. |
| 2018/0008830 A1 | | 1/2018 | Kaiser |
| 2018/0185652 A1 | | 7/2018 | Mika et al. |
| 2018/0235537 A1 | * | 8/2018 | Whiting ............... A61N 1/3621 |
| 2018/0279889 A1 | | 10/2018 | Lee |
| 2018/0359199 A1 | | 12/2018 | Nguyen et al. |
| 2019/0004879 A1 | | 1/2019 | Chang et al. |
| 2019/0005257 A1 | | 1/2019 | Diekmann et al. |
| 2019/0282298 A1 | | 9/2019 | Gertner |

FOREIGN PATENT DOCUMENTS

| | | |
|---|---|---|
| CN | 207707904 U | 8/2018 |
| KR | 20180024266 A | 3/2018 |
| WO | 2012169692 A1 | 12/2012 |
| WO | 2015094401 A1 | 6/2015 |
| WO | 2017117074 A1 | 7/2017 |
| WO | 2020096982 A1 | 5/2020 |

OTHER PUBLICATIONS

M. Birgersson, G. Hansson and U. Franke, "Data Integration Using Machine Learning," 2016 IEEE 20th International Enterprise Distributed Object Computing Workshop (EDOCW), Vienna, Austria, 2016, pp. 1-10, doi: 10.1109/EDOCW.2016.7584357.

Extended European Search Report in International Application No. PCT/US2020/044784, mailed Apr. 23, 2024 (6 pages).

International Search Report and Written Opinion in Application No. PCT/US2022/044784, dated Dec. 24, 2020 (8 pages).

B. Noll et al., "Influence of Pacing Mode and Rate on Peripheral Levels of Atrial Natriuretic Peptide (ANP)," Pace, Nov. 1989, vol. 12; pp. 1763-1768.

* cited by examiner

METHOD OF TREATMENT OF DRUG RESISTANT HYPERTENSION

CROSS-REFERENCE TO RELATED APPLICATIONS

This application is a U.S. national phase entry under 35 U.S.C. § 371 of International Application No. PCT/US2020/044784, filed on Aug. 3, 2020 which claims priority to, and the benefit of the earlier filing date of: U.S. provisional patent application entitled Method of Treatment of Drug Resistant Hypertension by Electrically Stimulating the Right Atrium to Create Inhibition of the Autonomic Nervous System, filed on May 5, 2020, Ser. No. 63/101,544, pursuant to 35 USC 119; is a continuation in part of PCT Patent Application, PCT/US2020/2547725447, filed on Mar. 27, 2020, which is an international patent application of and claims priority to U.S. provisional patent application 62/833,052, filed on Apr. 12, 2019; and is a continuation in part application of PCT/US2019/59703, filed on Nov. 4, 2019, which is a nonprovisional patent application of and claims priority to U.S. provisional patent applications 62/757,559, filed on Nov. 8, 2018 and 62/833,052 filed on Apr. 12, 2019, the contents of all of which are incorporated herein by reference.

BACKGROUND

Field of the Technology

The invention relates to methods and apparatus for treating diastolic heart failure and for controlling blood pressure in patients who have proven to be resistant to drug treatments for blood pressure control in the fields characterized by CPC A61N 1/36564; A6 1 N 11368.2; A6 1N 1/36585; A61N 1/36117; and A6 1N 1/36571.

Description of the Prior Art

We have previously disclosed a method to treat drug resistant hypertension and heart failure with preserved ejection fraction, aka diastolic heart failure. See, PCT Patent Applications entitled, "Method and Apparatus for Treatment of Drug Resistant Hypertension Associated with Impaired Left Ventricular Function and Bradycardia Using a Cardiac Pacemaker", PCT/US19/59703, and entitled "An Intelligently, Continuously and Physiologically Controlled Pacemaker and Method of Operation of the Same", PCT/US2020/25447, which are again incorporated herein by reference in their entirety.

That method comprises a blood pressure sensor connected via a secure Bluetooth or similar communication connection to an application containing an algorithm (referenced as PressurePace) that processes the blood pressure reading determining the optimal right atrial pacing rate of the pacemaker. The calculated atrial pacing rate is then transmitted to the pacemaker via an encrypted Bluetooth or similar connection to regulate the implanted pacemaker's right atrial pacing rate thereby optimizing blood pressure and treating diastolic heart failure.

It has been previously published by one of us, Dr. Eli Gang, that atrial subthreshold pacing can have an effect on local tissue refractory properties, such as the inhibition of impulse transmission across an accessory pathway in the heart of a patient.

In addition, there is ample evidence in the literature that non-propagated high intensity pacing stimuli delivered to the ventricle during refractoriness (i.e., during the R-wave) can enhance contractile properties of the ventricle.

It has been experimentally shown that atrial pacing can promote the secretion of a hormone produced by atrial tissue, namely, atrial natriuretic peptide, which has been shown to lower blood pressure under certain physiologic conditions. "Noll B, Krappe J, Göke B, Maisch B (1989) Influence of pacing mode and rate on peripheral levels of atrial natriuretic peptide (ANP). PACE 12:1763-1768, and Noll B, Krappe J, Göke B, Maisch B (1990) Atrial natriuretic peptide levels reflect hemodynamic changes under pacemaker stimulation. PACE 13:970-975.

However, there are no publications disclosing use of either subthreshold and/or non-propagated supra-threshold pacing algorithms in the right atrium designed to affect blood pressure via interaction with epicardial cardiac ganglia or other neuroendocrine mechanisms.

BRIEF SUMMARY

The illustrated embodiments of the invention include an apparatus used to treat drug resistant hypertension and heart failure with a preserved ejection fraction (aka diastolic heart failure). The apparatus includes a blood pressure measuring device, a cardiac pacemaker, and an application module containing two algorithms or software defined modules linking the blood pressure measuring device and the pacemaker. The measuring device, the pacemaker and application module are mutually communicated through encrypted Bluetooth or a similar wireless communication protocol. The first algorithm or module (hereinafter referenced as "PressurePace") calculates the optimal right atrial pacing rate of the cardiac pacemaker to optimally regulate a patient's blood pressure. The second algorithm or module (hereafter, referenced as the "Stimulus Architecture Algorithm" or "SAA") calculates the optimal stimulus output of the pacemaker's right atrial pacing electrode, namely such parameters as amplitude, pulse width, and frequency of subthreshold stimulations grouped into one bundled stimulus train to be delivered to the right atrial tissue to produce one paced heartbeat. This of right atrial stimulation causes feedback inhibition of cardiac-adjacent sympathetic and/or parasympathetic nervous system tissues, resulting in a lowering of blood pressure.

In summary, the illustrated embodiments of the invention include a method of right atrial pacing of a heart of a patient. The method includes the steps of: stimulating right atrial tissue of the heart using a right atrial lead of a dual chamber cardiac pacemaker to pace the heart with a stimulus architecture protocol; and stimulating local sympathetic and/or parasympathetic tissues with the stimulus architecture protocol proximate to the paced right atrial tissue causing nervous system activity that inhibits the autonomous nervous system to reduce blood pressure.

The step of stimulating right atrial tissue of the heart using a right atrial lead of a dual chamber cardiac pacemaker to pace the heart with a stimulus architecture protocol includes the step of stimulating right atrial tissue with a selected composite amplitude of the pacing stimulus, a selected number of sub-pulses within the pacing stimulus totaling the composite delivered amplitude, a selected frequency of the sub-pulses, a selected duration of the sub-pulses, and/or a selected refractory period before another impulse can be generated, where the selections are determined by an artificial intelligence derived stimulus architecture protocol.

The step of stimulating right atrial tissue of the heart and stimulating local sympathetic and/or parasympathetic tissues with the stimulus architecture protocol includes the step of stimulating the right atrial tissue of the heart and stimulating local sympathetic and/or parasympathetic tissues using an optimized stimulus protocol devised by artificial intelligence for the patient to reduce blood pressure selected from the group selectively varied stimulus amplitude, selectively varied stimulus duration, selectively varied the ascent and descent phase slopes of stimulation, selectively varied number of impulses delivered in a train or a succession of closely spaced stimuli, selectively varied frequencies of the impulses delivered as a train or a succession of closely spaced stimuli, and/or selectively varied amplitudes of the individual impulses delivered as a train or a succession of closely spaced stimuli, where intensity of delivered right atrial stimuli may be subthreshold or suprathreshold; and where the impulses may be propagated or nonpropagated, depending on the timing of the impulse, as determined by the stimulus architecture protocol.

The step of stimulating the right atrial tissue of the heart and stimulating local sympathetic and/or parasympathetic tissues using an optimized stimulus protocol devised by artificial intelligence for the patient to reduce blood pressure includes the steps of: determining if a cardiac beat is required; and supra-threshold pacing the heart and causing a neuro-inhibitory feedback to lower blood pressure, if a cardiac beat is required.

Alternatively the step of stimulating the right atrial tissue of the heart and stimulating local sympathetic and/or parasympathetic tissues using an optimized stimulus protocol devised by artificial intelligence for the patient to reduce blood pressure includes the steps of determining if a cardiac beat is required; and sub-threshold pacing the heart to only produce a neuro-inhibitory effect on blood pressure without pacing the heart, if a cardiac beat in not required.

The step of stimulating right atrial tissue of the heart and stimulating local sympathetic and/or parasympathetic tissues with the stimulus architecture protocol includes the step of stimulating the right atrial tissue with a right atrial pacing lead with multiple pacing electrodes such that one pacing electrode comprises a conventional right atrial pacing lead, and one or more other pacing electrodes are arranged and configured to be disposed anatomically proximate to atrial tissue proximate to sympathetic and/or parasympathetic ganglionic tissues for the purpose of stimulating those ganglionic tissues to lower blood pressure.

The scope of the invention also extends to include a closed loop system. The closed system includes: a blood pressure measuring device for transmitting a blood pressure reading; an applications module receiving the blood pressure reading from the applications module, where the applications module operates under an algorithm that uses the measured blood pressure reading to calculate a selected stimulus architecture of which selectively stimulates the right atrial tissue of the heart and selectively stimulates local sympathetic and/or parasympathetic tissues using an optimized stimulus protocol devised by artificial intelligence for the patient to control blood pressure; and a cardiac pacemaker communicated with the applications module to regulate right atrial pacing for the purpose of controlling blood pressure.

The pacemaker determines if a cardiac paced beat is required and the pacemaker applies supra-threshold pacing to the heart and causes a neuro-inhibitory feedback to lower blood pressure according to a stimulus architecture generated by the applications module, if a cardiac beat is required.

The pacemaker determines if a cardiac paced beat is required and the pacemaker applies sub-threshold pacing to the heart causing a neuro-inhibitory feedback back to lower blood pressure according to a stimulus architecture generated by the applications module, if a cardiac beat is not required.

The applications module includes a PressurePace module for first determining an optimal right atrial pacing rate and includes a Stimulus Architecture Algorithm module (SSA) to calculate the selected stimulus architecture based on the optimal right atrial pacing rate from the PressurePace module.

The applications module constructs an algorithm that uses the measured blood pressure reading to calculate a selected stimulus architecture algorithm for regulating right atrial pacing using artificial intelligence using the measured blood pressure reading.

The applications module constructs an algorithm that uses the measured blood pressure reading to calculate a selected stimulus architecture algorithm for regulating right atrial pacing using artificial intelligence using the measured blood pressure reading and at least input selected from the group of patient age, sex, medications, ambient temperature, altitude, patient's instantaneous reports of symptoms, or other parameters deemed relevant by the attending cardiologist.

Right atrial pacing for the purpose of lowering blood pressure is carried out via the multi-electrode pacing electrode, having at least one conventional right atrial pacing electrode and one or more other pacing electrodes arranged and configured to be disposed anatomically proximate to atrial tissue proximate to sympathetic and/or parasympathetic ganglionic tissues for the purpose of stimulating those ganglionic tissues to lower blood pressure.

Thus, the scope of the invention further extends to a cardiac pacing lead for stimulating right atrial tissue of the heart and stimulating local sympathetic and/or parasympathetic tissues with the stimulus architecture protocol including: a conventional right atrial pacing lead; and one or more other electrodes arranged and configured to be disposed anatomically proximate to atrial tissue proximate to sympathetic and/or parasympathetic ganglionic tissues for the purpose of stimulating those ganglionic tissues to lower blood pressure.

The conventional right atrial pacing lead and one or more other electrodes deliver a plurality of selected stimulus architectures to the right atrium of a heart which selectively stimulates the right atrial tissue of the heart and selectively stimulates local sympathetic and/or parasympathetic tissues respectively, using an optimized stimulus protocol devised by artificial intelligence for the patient to control blood pressure.

The conventional right atrial electrode delivers a suprathreshold pacing to the heart and at least one of the other electrodes causes a neuro-inhibitory feedback to lower blood pressure according to a stimulus architecture generated by the applications module, if a cardiac beat is required.

The conventional right atrial electrode delivers a subthreshold pacing to the heart and at least one of the other electrodes causes a neuro-inhibitory feedback to lower blood pressure according to a stimulus architecture generated by the applications module, if a cardiac beat is not required.

A pacing stimulus can be delivered on one electrode without delivery of a pacing stimulus being delivered on other electrodes.

The one or more other electrodes can deliver energy with a specific protocol to the right atrial tissue affecting blood pressure without inducing cardiac pacing.

The illustrated embodiments also extend to a closed loop system including: a skin sensor for real-time measurement of an ANS function to measure skin sympathetic or parasympathetic activity; an applications module receiving the real-time measurement of the ANS function, where the applications module operates under an algorithm that uses the real-time measurement of an ANS function to calculate a selected stimulus architecture of which selectively stimulates the right atrial tissue of the heart and selectively stimulates local sympathetic and/or parasympathetic tissues using an optimized stimulus protocol to control blood pressure; and a cardiac pacemaker communicated with the applications module to regulate right atrial pacing for the purpose of controlling blood pressure.

The applications module operates under an algorithm by using artificial intelligence to stimulate the right atrial tissue of the heart with the optimal stimulus protocol to control blood pressure.

The closed loop system further includes a blood pressure sensor, the blood pressure sensor and skin sensor communicated with the applications module.

The closed loop system in one embodiment is combined with a smartphone, and the skin sensor is communicated with the applications module through the smartphone.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE PREFERRED EMBODIMENTS

This application expands on the use of either subthreshold and/or non-propagated supra-threshold pacing algorithms in the right atrium designed to affect blood pressure via interaction with epicardial cardiac ganglia or other neuroendocrine mechanisms by means of atrial natriuretic peptides by delivering the pacing impulse to the right atrial tissue. The pacing impulse activates the local sympathetic and/or parasympathetic ganglia producing a neural feedback that results in suppression of blood pressure. A supra-threshold pacing algorithm means the pacing stimuli cause a paced beat unless placed somewhere outside the vulnerable zone of tissue. The pacing stimuli could also be a train of stimuli, none of which is individually supra-threshold, but in aggregate are supra-threshold in total voltage.

It cannot currently be determined as a certainty whether we are stimulating sympathetic, parasympathetic nerve endings, an interplay between the two, or none of the above. Both sympathetic and parasympathetic nerve endings are found in cardiac ganglia. Therefore, where sympathetic tissue is referenced, it is to be understood throughout t this specification that both sympathetic and/or parasympathetic nerve activity may be present, possibly by affecting epicardial ganglionated plexi. In particular, it must be understood that both sympathetic and parasympathetic inputs to the heart are provided.

Figure 1:
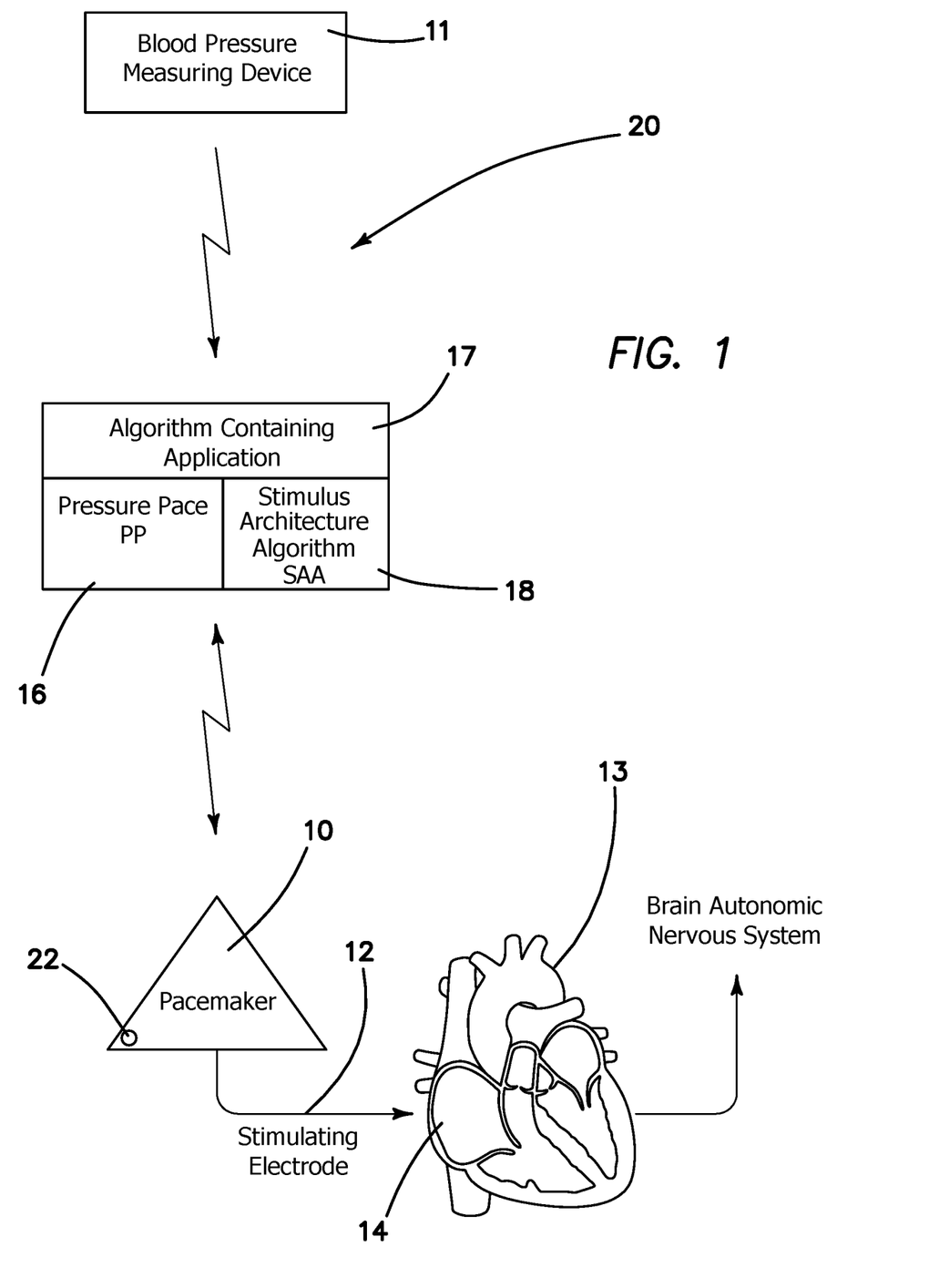
FIG. 1 is a block diagram illustrating the main elements of an embodiment of the invention.

The illustrated embodiment of the invention as diagrammatically depicted in FIG. 1 includes: (a) a pacemaker 10 with a pacing electrode 12 implanted in the right atrium 14 of heart 13, and (b) an algorithmic module 17 that determines the (c) stimulus architecture or protocol delivered through the pacing electrode 12 into the right atrial tissue 14. In one embodiment, the pacing electrode 12 is a conventional right atrial pacing electrode. After receiving the blood pressure reading wirelessly transmitted from blood pressure sensor 11, the PressurePace algorithm or module 16 calculates the optimal right atrial pacing rate as more fully described in the incorporated patent applications. The optimal right atrial pacing rate is then further processed by the Stimulus Architecture Algorithm (SAA) module 18 to arrive at the optimal stimulus protocol or format. The optimal stimulus protocol determines the composite amplitude of the pacing stimulus, the number of sub-pulses within the pacing stimulus totaling the composite delivered amplitude, the frequency of the sub-pulses, the duration of the sub-pulses, and the refractory period before another impulse can be generated.

Figure 3:
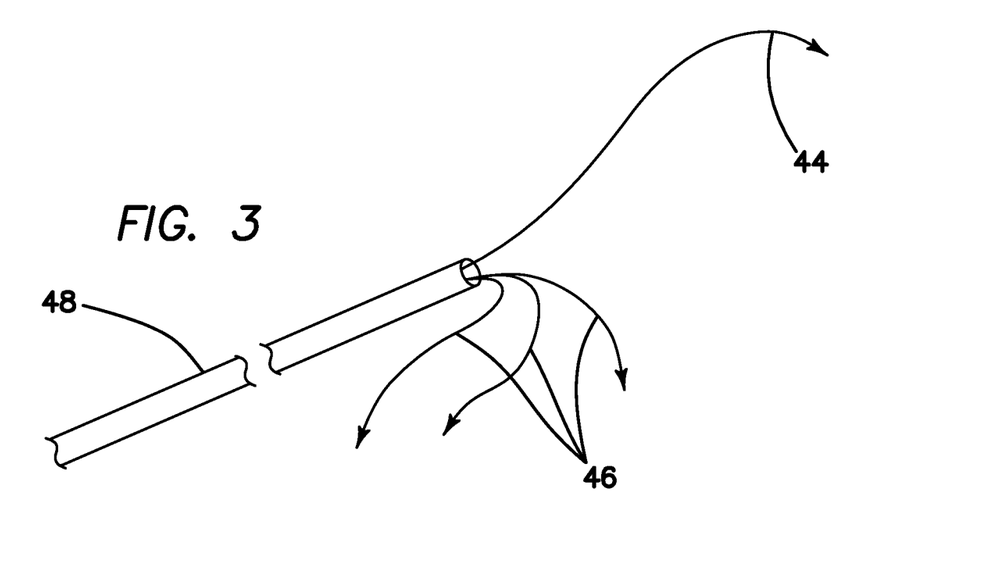
FIG. 3 is a simplified diagram of one embodiment of a cardiac lead used in the illustrated embodiment of the invention.

A schematic diagram of the illustrated embodiment of the invention is presented in the diagram of FIG. 1. The components of the system 20 can vary, but essential elements include the pacing electrode 12. In other embodiments of the invention the pacing electrode 12 may comprise a plurality of electrodes, which include deliver stimulating pulses to more than one site, where the second or multiple stimulation sites, which can be single or an array, are designed to be positioned closer to the local sympathetic and/or parasympathetic ganglia to more optimally stimulate those autonomic nervous system tissues to produce a neuro-inhibitory effect on blood pressure. FIG. 3 is a simplified diagram of one embodiment of such a multiple electrode lead 48, including a conventional right atrial cardiac lead 44 and a plurality of other neuro-inhibitory leads 46.

System 20 further includes the SAA algorithm or module 18. The SAA algorithm or module 18 uses computational and artificial intelligence analysis methods to determine the optimal stimulus protocol. The optimal stimulus architecture is computed by the SAA algorithm or module 18 to optimally regulate the neuro-inhibitory component of the right atrial pacing effect, taking into account other simultaneous factors including pacemaker rate modulation sensor outputs, e.g. from accelerometer and respiratory rate sensor 22 included in pacemaker 10, and the PressurePace-derived optimal right atrial pacing rate. In alternative embodiments of the PressurePace algorithm or module 16, this will include additional factors previously described in the incorporated patent applications, including but not limited to patient age, sex, medications, ambient temperature, altitude, patient's instantaneous reports of symptoms, and any other parameters deemed relevant by the attending cardiologist.

Figure 2:
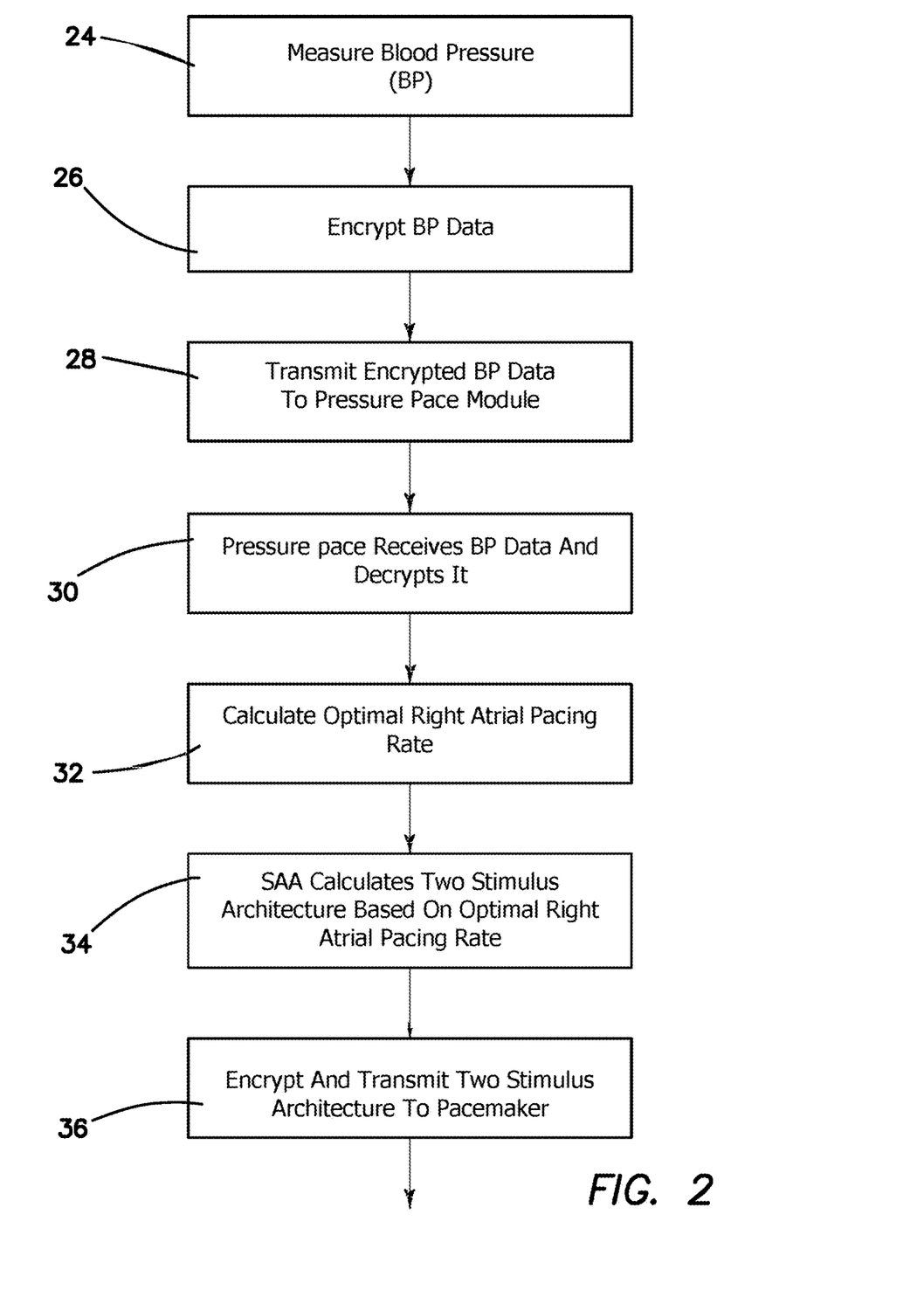
FIG. 2 is a flow diagram illustrating one embodiment of the methodology of the invention.

The illustrated embodiment of the methodology is better understood by turning the flow diagram of FIG. 2. At step 24 the patient's blood pressure (BP) is measured using a blood pressure measuring device. The measured blood pressure data is then encrypted at step 26. The encrypted BP data is wirelessly transmit data to the PressurePace software module 16 at step 28. The PressurePace software module 16 receives data and decrypts it at step 30. At step 32 the PressurePace module 16 calculates an optimal right atrial pacing rate, based on a determination made by the corresponding algorithm using artificial intelligence (AI) as set out in the incorporated patent applications.

Computer science defines AI research as the study of "intelligent agents": any device that perceives its environment and takes actions that maximize its chance of successfully achieving its goals. A more elaborate definition characterizes AI as "a system's ability to correctly interpret external data, to learn from such data, and to use those learnings to achieve specific goals and tasks through flexible adaptation. A typical AI analyzes its input data and takes actions that maximize its chance of success, in this case reduction of blood pressure. AI often revolves around the use of algorithms. An algorithm is a set of unambiguous instructions that a mechanical computer can execute. A complex algorithm is often built on top of other, simpler, algorithms. Many AI algorithms are capable of learning from data; they can enhance themselves by learning new heuristics (strategies, or "rules of thumb", that have worked well in the past), or can themselves write other algorithms. Some of the "learners" described below, including Bayesian networks, decision trees, and nearest-neighbor, could theoretically, (given infinite data, time, and memory) learn to approximate any function, including which combination of mathematical functions would best describe the world. These learners could therefore derive all possible knowledge, by considering every possible hypothesis and matching them against the data. In practice, it is seldom possible to consider every possibility, because of the phenomenon of "combinatorial explosion", where the time needed to solve a problem grows exponentially. Much of AI research involves figuring out how to identify and avoid considering a broad range of possibilities unlikely to be beneficial.

The earliest (and easiest to understand) approach to AI was symbolism (such as formal logic): "If an otherwise healthy adult has a fever, then they may have influenza". A second, more general, approach is Bayesian inference: "If the current patient has a fever, adjust the probability they have influenza in such-and-such way". The third major approach, extremely popular in routine business AI applications, are analogizers such as support vector machine model (SVM) and nearest-neighbor: "After examining the records of known past patients whose temperature, symptoms, age, and other factors mostly match the current patient, X % of those patients turned out to have influenza". A fourth approach is harder to intuitively understand, but is inspired by how the brain's machinery works: the artificial neural network approach uses artificial "neurons" that can learn by comparing itself to the desired output and altering the strengths of the connections between its internal neurons to "reinforce" connections that seemed to be useful. These four main approaches can overlap with each other and with evolutionary systems; for example, neural nets can learn to make inferences, to generalize, and to make analogies. Some systems implicitly or explicitly use multiple of these approaches, alongside many other AI and non-AI algorithms; the best approach is often different depending on the problem.

Learning algorithms work on the basis that strategies, algorithms, and inferences that worked well in the past are likely to continue working well in the future. These inferences can be obvious, such as "since the sun rose every morning for the last 10,000 days, it will probably rise tomorrow morning as well". They can be nuanced, such as "X % of families have geographically separate species with color variants, so there is a Y % chance that undiscovered black swans exist". Learners also work on the basis of "Occam's razor": The simplest theory that explains the data is the likeliest. Therefore, according to Occam's razor principle, a learner must be designed such that it prefers simpler theories to complex theories, except in cases where the complex theory is proven substantially better.

Settling on a bad, overly complex theory gerrymandered to fit all the past training data is known as overfitting. Many systems attempt to reduce overfitting by rewarding a theory in accordance with how well it fits the data, but penalizing the theory in accordance with how complex the theory is.[72] Besides classic overfitting, learners can also disappoint by "learning the wrong lesson". A toy example is that an image classifier trained only on pictures of brown horses and black cats might conclude that all brown patches are likely to be horses. A real-world example is that, unlike humans, current image classifiers don't determine the spatial relationship between components of the picture; instead, they learn abstract patterns of pixels that humans are oblivious to, but that linearly correlate with images of certain types of real objects. Faintly superimposing such a pattern on a legitimate image results in an "adversarial" image that the system misclassifies.

Stimulus architecture algorithm module (SAA) 18 calculates two different possible stimulus architectures at step 34. The first stimulus architecture includes a supra-threshold stimulus (cardiac pacing is required), which produces both cardiac pacing and stimulation of local sympathetic and/or parasympathetic tissues to produce feedback inhibition of the autonomic nervous system to lower blood pressure. The second stimulus architecture includes sub-threshold stimulus (cardiac pacing is not required) which produces only feedback inhibition of the autonomic nervous system to lower blood pressure.

The two stimulus architectures are encrypted and transmitted at step 36 wirelessly to a pacemaker 10 which is "paired" to receive and decrypt the signal only from stimulus architecture algorithm module (SAA) 18. Then at step 38 pacemaker 10 receives and decrypts the two stimulus architectures.

If the pacemaker programming determines at step 38 that a paced cardiac beat is indicated per standard pacemaker protocol, right atrial stimulation proceeds according to the first of the stimulus architectures at step 40, namely a supra-threshold stimulus (cardiac pacing is required), which produces both cardiac pacing and stimulation of local sympathetic and/or parasympathetic tissues to produce feedback inhibition of the autonomic nervous system to lower blood pressure. If the pacemaker programming determines that a paced cardiac beat is not required at step 38, right atrial stimulation proceeds at step 42 according to the second of the stimulus architectures, namely sub-threshold stimulus (cardiac pacing is not required) which produces only feedback inhibition of the autonomic nervous system to lower blood pressure.

We have previously disclosed in the incorporated applications the relationship between right atrial (RA) pacing and the treatment of dialysis-related hypotension (DRH) and diastolic heart failure (DHF). We have further described an automatic closed-loop system controlled by an algorithm, PressurePace (PP), comprised of a blood pressure measuring device connected via Bluetooth to a processor containing the PP algorithm such as a smartphone with Bluetooth, that is in turn connected via Bluetooth to a pacemaker to regulate RA pacing. We have suggested a mechanism of action for that system and a mechanical design thereto that involves direct stimulation of the autonomic nervous system (ANS) that does not require the provocation of a paced beat, so called subthreshold pacing controlled by a second algorithm we have called Stimulus Architecture Algorithm (SAA).

Also disclosed is an embodiment, which is an extension of the system described above and which integrates the real-time measurement of ANS function by adding a non-invasive skin sensor to the loop that measures skin sympathetic or parasympathetic activity. In one embodiment the ANS skin sensor is disposed on the back of a smartwatch worn in contact with the patient's skin. The smartwatch is communicated with a smartphone or a computer either by a cable or Bluetooth connection. Turn now and consider the measurement of skin sympathetic or parasympathetic activity (SKNA). SKNA directly and non-invasively records sympathetic or parasympathetic nerve activity. It can be used to measure sympathetic or parasympathetic tone in healthy subjects and in subjects with non-cardiovascular diseases. The electrical activity that can be measured on the surface of the skin originates from the heart, the muscle or nerve structures. Because the frequency content of nerve activity falls in a higher frequency range than that of the ECG and myopotentials, it is necessary to use high-pass or band-pass filtering to specifically isolate the SKNA signal. SKNA is voltage calibrated and does not require invasive procedures to invasively dispose electrodes in nerves and thus has advantages over microneurography. The measurement of SKNA can be performed using commercially available hardware and software.

Figure 4:
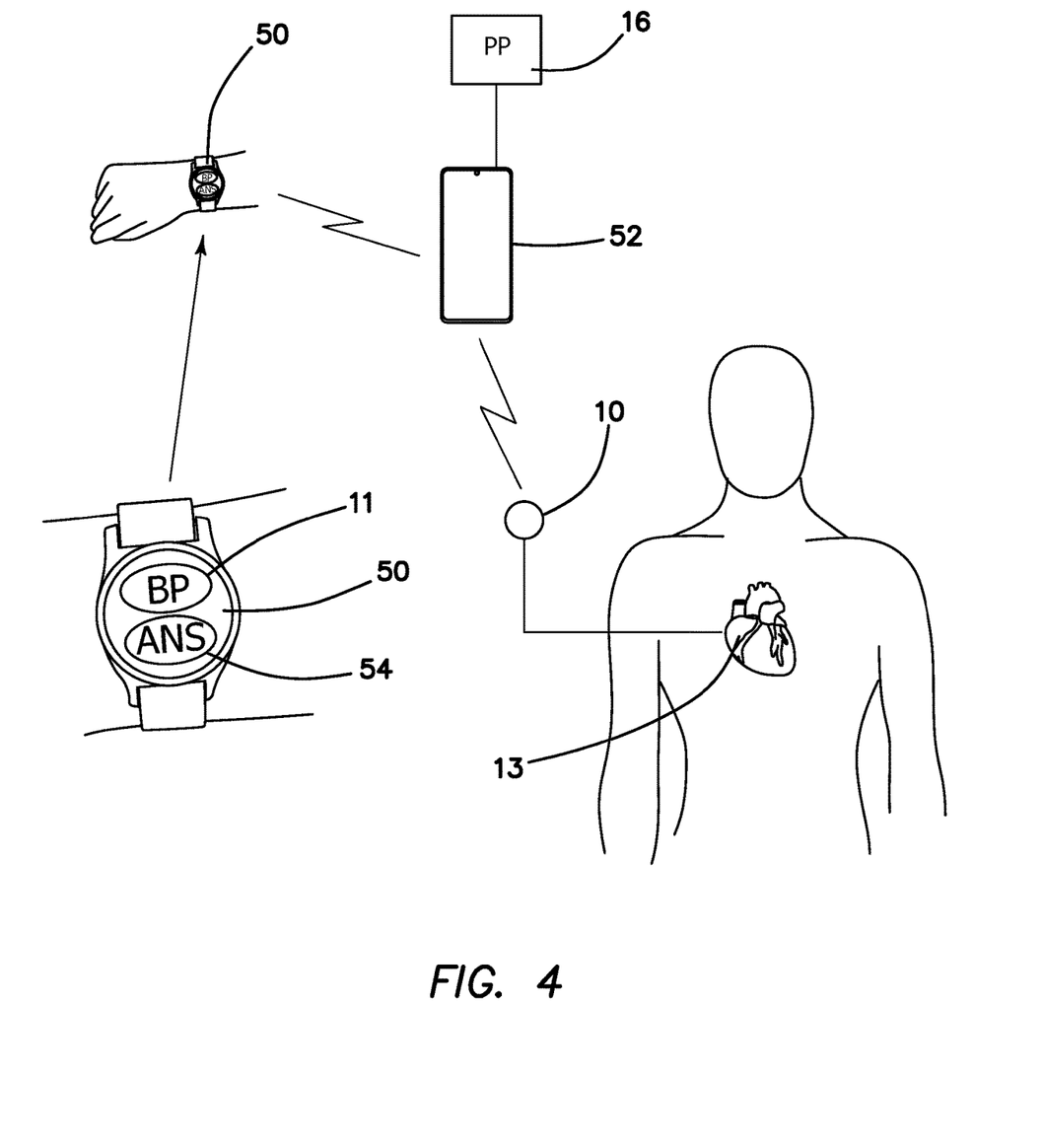
FIG. 4 is a diagram illustrating the SKNA sensing watch or bracelet with a blood pressure sensor communicated to the pacemaker with the possible intermediation of the PressurePace algorithm app and artificial intelligence processing.

An electrode (sensor) that can receive the SKNA signal is affixed or otherwise affixed to the bottom surface of a non-pneumatic driven blood pressure sensing watch 50 as is currently available and FDA approved diagrammatically illustrated in FIG. 4. This configuration places the electrode in contact with the wearer's skin when the watch is worn on the wrist or other suitable body part. The watch 50 is Bluetooth enabled and configured to communicate with the PressurePace app 16. The watch 50 also contains electronic elements that process the skin electrode's signal as previously described and validated. The same electrode may also be used to receive the patient's ECG for other applications, including other versions of PressurePace algorithm that may include an ECG signal as part of the dataset.

In the preferred embodiment, the watch 50 encrypts both the blood pressure result and the skin sensor output and sends those results to the PressurePace application 16 which is resident in a smart phone 52 that has been paired with watch 50 to receive the processed SKNA signals. As previously described, the PressurePace app 16 decrypts both signals and calculates the optimal RA pacing rate to both lower blood pressure and, in the present embodiment, optimize the sympathetic tone, peripheral resistance or systemic vascular resistance as a secondary factor in regulating blood pressure. The resultant RA pacing command is then encrypted and sent via Bluetooth to the patient's pacemaker 10 which is capable of receiving the signal. It is decrypted and the command executed, thereby lowering blood pressure to the most efficient level, and also benefiting the treatment of heart failure with preserved ejection fraction (HFpEF). The process repeats every three minutes, or as otherwise programmed by the supervising physician.

Other embodiments include a version of blood pressure watch 50, which contains the blood pressure sensing sensor 11, the autonomous nervous system (ANS) sensor or electrode 54, and the PP app 16. Watch 50 may also include a separate ECG sensing electrode with the ANS sensor or electrode 54 and the PP app 16.

i. In another embodiment the blood pressure measuring device is a conventional pneumatic cuff with Bluetooth capability, and the ANS sensor or electrode 54 is separate and worn separately on the wrist with Bluetooth capability to be sent to the app 16 which is in a smart phone 52. The ANS sensor or electrode 54 is optionally connected to the smartphone 52 via a wire cable that transmits the data. It must be understood that watch 50 may be provided with a variety different kinds of sensing mechanisms and combinations with smartphone 52 and PP app 16 with or without artificial intelligence processing described above. For example, the blood pressure sensor may or may include a manual or automatic pneumatic cuff or may be electronic, may or may not be Bluetooth communicated to the smartphone 52, may or may not be an implanted blood pressure sensor, may or may not have an ANS sensor 54, may be carried separately in a bracelet with or without Bluetooth communication or hardwired cable communication to smartphone 52, may or may not have PP app 16 resident in watch 50, in other blood pressure devices, in smartphone 52, in a separate processing module, or in pacemaker 10. Thus, it is clear it is entirely within the scope of the invention that the elements including watch 50 or a substitute bracelet (not shown), smartphone 52, ANS sensor 54, PP app 16, and pacemaker 10 may be combined in a large number of different equivalent permutations and intercommunicated by Bluetooth or cable with or without artificial intelligence processing.

Many variations and modifications may be made by those having ordinary skill in the art without departing from the spirit and scope of the embodiments. Therefore, it must be understood that the illustrated embodiment has been set forth only for the purposes of example and that it should not be taken as limiting the embodiments as defined by the following embodiments and its various embodiments.

Therefore, it must be understood that the illustrated embodiment has been set forth only for the purposes of example and that it should not be taken as limiting the embodiments as defined by the following claims. For example, notwithstanding the fact that the elements of a claim are set forth below in a certain combination, it must be expressly understood that the embodiments includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the embodiments.

We claim:

1. A method for determining stimulus protocols, the method comprising:
   receiving a physiological input value;
   calculating a pacing rate based on the physiological input value;
   determining a supra-threshold stimulus protocol to produce cardiac pacing and stimulation of one or both of local sympathetic tissue or parasympathetic tissues to modify the physiological input value, based on the pacing rate;
   determining a sub-threshold stimulus protocol to produce feedback inhibition of a portion of an autonomic nervous system to modify the physiological input value, based on the pacing rate;
   determining, for each of the supra-threshold stimulus protocol and the sub-threshold stimulus protocol, a respective composite amplitude of pacing stimulus, frequency of sub-pulses, duration of sub-pulses, and refractory period between a current pacing stimulus and a subsequent pacing stimulus; and
   transmitting, to a pacemaker for pacing a heart, the supra-threshold stimulus protocol and the sub-threshold stimulus protocol, wherein the pacemaker is configured to pace the heart at a new pacing rate based on the supra-threshold stimulus protocol or the sub-threshold stimulus protocol and based on the respective composite amplitude of pacing stimulus, frequency of sub-pulses, duration of sub-pulses, and refractory period.

2. The method of claim 1, wherein the respective composite amplitude of pacing stimulus is reached based on a number of sub-pulses, the number of sub-pulses having amplitudes totaling the composite amplitude of pacing stimulus.

3. The method of claim 1, further comprising causing a pacing device to apply one of the supra-threshold stimulus based on determining that a paced cardiac beat is required or the sub-threshold stimulus based on determining that a paced cardiac beat is not required.

4. The method of claim 1, wherein the physiological input value is a blood pressure value.

5. The method of claim 1, wherein calculating the pacing rate comprises:
   comparing the physiological input value to a target physiological input value; and determining the pacing rate based on comparing the physiological input value to the target physiological input value.

6. The method of claim 1, wherein calculating the pacing rate comprises:
   comparing the physiological input value to a target physiological input value; and determining the pacing rate based on comparing the physiological input value to the target physiological input value, and wherein the target physiological input value is based on one or more of a patient state, a patent demographic, a patient medication, an ambient condition, or a patient symptom.

7. The method of claim 1, further comprising: receiving a skin sympathetic or parasympathetic activity; and calculating the pacing rate further based on the skin sympathetic or parasympathetic activity.

8. The method of claim 1, further comprising: receiving a skin sympathetic or parasympathetic activity; and calculating the pacing rate further based on the skin sympathetic or parasympathetic activity, wherein the skin sympathetic or parasympathetic activity is received from at least one of a high-pass or a band-pass filter.

9. The method of claim 1, further comprising:
   receiving autonomic nervous system (ANS) activity from one of a direct sensor or an indirect function; and
   calculating the pacing rate further based on the ANS activity.

10. The method of claim 1, further comprising:
    receiving autonomic nervous system (ANS) activity from one of a direct sensor or an indirect function; and
    calculating the pacing rate further based on the ANS activity, wherein one or both of the supra-threshold stimulus protocol or the sub-threshold stimulus protocol are output by an artificial intelligence (AI) model.

11. The method of claim 1, receiving autonomic nervous system (ANS) activity from one of an direct sensor or an indirect function; and
    calculating the pacing rate further based on the ANS activity, wherein one or both of the supra-threshold stimulus protocol or the sub-threshold stimulus protocol are output by an artificial intelligence (AI) model, wherein the AI model is trained to output a stimulus protocol based on training data comprising the physiological input value and one or more of ANS activity, a patient age, a patient sex, a patient medication, an ambient temperature, or a patient symptom.

12. A method for determining stimulus protocols, the method comprising:
    receiving a physiological input value;
    calculating a pacing rate based on the physiological input value;

receiving one of an indication that a paced cardiac beat is required or that a paced cardiac beat is not required;

determining, based on receiving the indication that the paced cardiac beat is required, a supra-threshold stimulus protocol to produce cardiac pacing and stimulation of one or both of local sympathetic tissue or parasympathetic tissues to modify the physiological input value, based on the pacing rate;

determining for the supra-threshold stimulus protocol, a first composite amplitude of pacing stimulus, a first frequency of sub-pulses, a first duration of sub-pulses, and a first refractory period between a current pacing stimulus and a subsequent pacing stimulus;

determining, based on receiving the indication that the paced cardiac beat is not required, a sub-threshold stimulus protocol to produce feedback inhibition of a portion of an autonomic nervous system to modify the physiological input value based on the pacing rate determining, for the sub-threshold stimulus protocol, a second composite amplitude of pacing stimulus, a second frequency of sub-pulses, a second duration of sub-pulses, and a second refractory period between a current pacing stimulus and a subsequent pacing stimulus; and transmitting, to a pacemaker for pacing a heart, the supra-threshold stimulus protocol or the sub-threshold stimulus protocol, wherein the pacemaker is configured to pace the heart at a new pacing rate based on the supra-threshold stimulus protocol or the sub-threshold stimulus protocol.

13. The method of claim 12, wherein the one of the indication that a paced cardiac beat is required or that the paced cardiac beat is not required is based on a pacing device protocol.

14. The method of claim 12, further comprising providing the supra-threshold stimulus protocol if the indication that the paced cardiac beat is required, is received.

15. The method of claim 12, further comprising providing the sub-threshold stimulus protocol if the indication that the paced cardiac beat is not required, is received.

* * * * *